(12) United States Patent
Kramer et al.

(10) Patent No.: US 9,656,039 B2
(45) Date of Patent: May 23, 2017

(54) BREATHING ASSISTANCE APPARATUS WITH A MANIFOLD TO ADD AUXILIARY GASES TO AMBIENT GASES

(71) Applicant: Fisher & Paykel Healthcare Limited, Auckland (NZ)

(72) Inventors: Martin Paul Friedrich Kramer, Auckland (NZ); Kevin Peter O'Donnell, Auckland (NZ); Christopher Simon James Quill, Auckland (NZ); Matthew Jon Payton, Auckland (NZ)

(73) Assignee: Fisher & Paykel Healthcare Limitied, Auckland (NZ)

( * ) Notice: Subject to any disclaimer, the term of this patent is extended or adjusted under 35 U.S.C. 154(b) by 333 days.

(21) Appl. No.: 14/286,590

(22) Filed: May 23, 2014

(65) Prior Publication Data

US 2014/0345615 A1 Nov. 27, 2014

Related U.S. Application Data

(63) Continuation of application No. 11/916,503, filed as application No. PCT/NZ2006/000166 on Jun. 29, 2006, now Pat. No. 8,733,353.

(30) Foreign Application Priority Data

Jul. 1, 2005 (NZ) ........................ 541083

(51) Int. Cl.
*A61M 16/16* (2006.01)
*A61M 16/10* (2006.01)
(Continued)

(52) U.S. Cl.
CPC .... *A61M 16/1005* (2014.02); *A61M 16/0066* (2013.01); *A61M 16/10* (2013.01);
(Continued)

(58) Field of Classification Search
CPC .. A61M 11/00; A61M 11/005; A61M 11/042; A61M 11/06; A61M 11/065;
(Continued)

(56) References Cited

U.S. PATENT DOCUMENTS 3,714,944 A  2/1973  Price et al.
3,863,630 A  2/1975  Cavallo
(Continued)

FOREIGN PATENT DOCUMENTS

DE  43 27 730  3/1995
DE  196 21 541  4/1997
(Continued)

*Primary Examiner* — Annette Dixon
(74) *Attorney, Agent, or Firm* — Knobbe, Martens, Olson & Bear, LLP.

(57) ABSTRACT

The breathing assistance apparatus of the present invention includes a manifold that is provided with or retrofittable to gases supply and humidifying devices. The manifold allows gases from an oxygen concentrator to be combined with the flow through a gases supply and humidifying device, most usually air The combined output of oxygen and other breathing gases (air) is then humidified. The breathing assistance apparatus and manifold of the present invention provides a safe method to add oxygen to the input air stream of a gases supply and humidifying device and reduces the amount of accumulation of oxygen within the gases supply device, reducing fire risk should sparking occur within the device.

19 Claims, 4 Drawing Sheets

(51) Int. Cl.
*A61M 16/12* (2006.01)
*A61M 16/00* (2006.01)
*A61M 16/06* (2006.01)

(52) U.S. Cl.
CPC ........ *A61M 16/105* (2013.01); *A61M 16/109* (2014.02); *A61M 16/1075* (2013.01); *A61M 16/1095* (2014.02); *A61M 16/12* (2013.01); *A61M 16/16* (2013.01); *A61M 16/0666* (2013.01)

(58) Field of Classification Search
CPC .............. A61M 15/0091; A61M 16/00; A61M 16/0051; A61M 16/0057; A61M 16/0063; A61M 16/0066; A61M 16/0069; A61M 16/0096; A61M 16/0465; A61M 16/0497; A61M 16/06; A61M 16/0627; A61M 16/08; A61M 16/10; A61M 16/1015; A61M 16/104; A61M 16/1085; A61M 16/109; A61M 16/12; A61M 16/125; A61M 16/127; A61M 16/16; A61M 16/161; A61M 16/18; A61M 16/20; A61M 16/202; A61M 16/205; A61M 16/206; A61M 16/208; A61M 16/22; A61M 2016/0021; A61M 2016/0027; A61M 2016/0036; A61M 2016/0039; A61M 2016/0042; A61M 2016/0063; A61M 2016/0069; A61M 2016/1025; A61M 2016/161; A61M 2202/0208; A61M 2205/16; A61M 2205/18; A61M 2205/3331; A61M 2205/3365; A61M 2205/3368; A61M 2205/3561; A61M 2205/3569; A61M 2205/3584; A61M 2205/3592; A61M 2205/36; A61M 2205/3653; A61M 2205/42; A61M 2205/502; A61M 2205/581; A61M 2205/587; A61M 2205/70; A61M 2205/8212; A61M 2230/205; A61M 2230/432; A61M 2230/435; A61M 2230/50; A61M 2230/60; A61M 2230/65; A63B 23/18
USPC ............ 128/200.14, 200.18, 200.21, 200.24, 128/201.13, 203.12, 203.14, 203.16, 128/203.17, 203.25, 203.26, 203.27, 128/204.13, 204.17, 204.18, 204.21, 128/204.22, 204.23, 204.24, 204.25, 128/205.11, 205.24, 205.25, 205.26, 128/207.14, 207.16, 207.18; 122/13.01, 122/13.3–19.2, 33, 487, 4 A, 5.5 A, 7 A
See application file for complete search history.

(56) References Cited

U.S. PATENT DOCUMENTS

| | | | |
|---|---|---|---|
| 3,894,537 A | 7/1975 | Camp | |
| 3,915,386 A | 10/1975 | Vora | |
| 4,159,803 A * | 7/1979 | Cameto | B05B 17/0615 239/102.2 |
| 4,198,969 A * | 4/1980 | Virag | A61M 11/06 128/200.21 |
| 4,427,004 A * | 1/1984 | Miller | A61M 11/06 128/200.21 |
| 4,622,963 A | 11/1986 | Ansite | |
| 4,708,831 A | 11/1987 | Elsworth et al. | |
| 4,776,990 A | 10/1988 | Verity | |
| 4,911,157 A | 3/1990 | Miller | |
| 5,101,820 A | 4/1992 | Christopher | |
| 5,237,987 A | 8/1993 | Anderson et al. | |
| 5,301,662 A | 4/1994 | Bagwell et al. | |
| 5,848,591 A | 12/1998 | Weismann | |
| 5,862,802 A | 1/1999 | Bird | |
| 5,931,159 A | 8/1999 | Suzuki et al. | |
| 5,954,050 A | 9/1999 | Christopher | |
| 6,041,776 A | 3/2000 | Briggs, III | |
| 6,435,180 B1 * | 8/2002 | Hewson | A61M 16/16 128/203.12 |
| 6,467,477 B1 | 10/2002 | Frank et al. | |
| 7,516,740 B2 | 4/2009 | Meler | |
| 8,733,353 B2 * | 5/2014 | Kramer | A61M 16/10 128/200.24 |
| 2004/0221844 A1 | 11/2004 | Hunt et al. | |
| 2007/0144514 A1 | 6/2007 | Yeates et al. | |
| 2009/0071478 A1 | 3/2009 | Kalfon | |

FOREIGN PATENT DOCUMENTS

| | | |
|---|---|---|
| EP | 0 117 699 | 9/1984 |
| GB | 2 154 467 | 9/1985 |
| GB | 2 201 602 | 9/1988 |
| WO | WO 97/13540 | 4/1997 |
| WO | WO 03/024505 | 3/2003 |

* cited by examiner

BREATHING ASSISTANCE APPARATUS WITH A MANIFOLD TO ADD AUXILIARY GASES TO AMBIENT GASES

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. application Ser. No. 11/916,503, filed Feb. 11, 2008, which is a National Phase filing of PCT/NZ2006/000166, having an International filing date of Jun. 29, 2006, which claims priority to New Zealand Application No. 541083 filed on Jul. 1, 2005. Each of the aforementioned patents/applications is hereby incorporated by reference.

BACKGROUND OF THE INVENTION

Field of the Invention

This invention relates to a gases supply and gases humidification apparatus including a manifold that allows for the addition of oxygen to the gases supply.

Description of the Related Art

A number of methods are known in the art for assisting a patient's breathing. Continuous Positive Airway Pressure (CPAP) involves the administration of air under pressure to a patient, usually by a nasal mask. It is used in the treatment of snoring and Obstructive Sleep Apnoea (OSA), a condition characterized by repetitive collapse of the upper airway during inspiration. Positive pressure splints the upper airway open, preventing its collapse. Treatment of OSA with nasal CPAP has proven to be both effective and safe, but CPAP is difficult to use and the majority of patients experience significant side effects, particularly in the early stages of treatment.

Upper airway symptoms adversely affect treatment with CPAP. Mucosal drying is uncomfortable and may awaken patients during the night. Rebound nasal congestion commonly occurs during the following day, simulating a viral infection. If untreated, upper airway symptoms adversely affect rates of CPAP use.

Increases in nasal resistance may affect the level of CPAP treatment delivered to the pharynx, and reduce the effectiveness of treatment. An individual pressure is determined for each patient using CPAP and this pressure is set at the patient interface. Changes in nasal resistance affect pressure delivered to the pharynx and if the changes are of sufficient magnitude there may be recurrence of snoring or airway collapse or reduce the level of pressure applied to the lungs.

CPAP is also commonly used for treatment of patients with a variety of respiratory illnesses or diseases, including Chronic Obstructive Pulmonary Disease (COPD).

Oxygen is the most common drug prescribed to hospitalized patients with respiratory or other illnesses. The delivery of oxygen via nasal cannula or facemask is of benefit to a patient complaining of breathlessness. By increasing the fraction of inspired oxygen, oxygen therapy reduces the effort to breathe and can correct resulting hypoxia (a low level of oxygen in the tissues).

The duration of the therapy depends on the underlying illness. For example, postoperative patients may only receive oxygen while recovering from surgery while patients with COPD require oxygen 16 to 18 hours per day.

Currently greater than 16 million adults are afflicted with COPD, an umbrella term that describes a group of lung diseases characterized by irreversible airflow limitation that is associated mainly with emphysema and chronic bronchitis, most commonly caused by smoking over several decades. When airway limitation is moderately advanced, it manifests as perpetual breathlessness without physical exertion. Situations such as a tracheobronchial infection, heart failure and also environmental exposure can incite an exacerbation of COPD that requires hospitalization until the acute breathlessness is under control. During an acute exacerbation of COPD, the patient usually experiences an increase in difficulty of breathing (dyspnea), hypoxia, and increase in sputum volume and purulence and increased coughing.

Oxygen therapy provides enormous benefit to patients with an acute exacerbation of COPD who are hypoxic, by decreasing the risk of vital organ failure and reducing dyspnea. The major complication associated with oxygen therapy is hypercarpnia (an elevation in blood carbon dioxide levels) and subsequent respiratory failure. Therefore, the dose of oxygen administered is important.

To accurately control an oxygen dose given to a patient, the oxygen-enriched gas must exceed the patient's peak inspiratory flow to prevent the entrainment of room air and dilution of the oxygen. To achieve this, flows of greater than 20 L/min are common. Such flows of dry gases cause dehydration and inflammation of the nasal passages and airways if delivered by nasal cannula. To avoid this occurrence, a heated humidifier may be used.

The majority of systems that are used for oxygen therapy or merely delivery of gases to a patient consists of a gases supply, a humidifier and conduit. Interfaces include facemasks, oral mouthpieces, tracheostomy inlets and nasal cannula, the latter then having the advantage of being more comfortable and acceptable to the patient than a facemask.

It is usual for the gases supply to provide a constant, prescribed level of gases flow to the humidifier. The humidifier and conduit can then heat and humidify the gases to a set temperature and humidity before delivery to the patient. Many patients using blowers or continuous positive pressure devices to treat COPD are on long term oxygen therapy. Such patients often need in excess of 15 hours per day of oxygen therapy and as such the only practical method to expose these patients to several hours humidification therapy per day as well as oxygen therapy is to combine the oxygen therapy and humidification therapy. As the oxygen therapy is known to dry the airways there are likely to be benefits from combining the treatments.

Currently CPAP systems are commonly integrated with oxygen flow systems to provide increased fraction of oxygen for the treatment of respiratory disorders. These systems commonly combine the oxygen source on the high pressure (flow outlet) side of the blower. This results in three main disadvantages. Firstly, by integrating the oxygen on the high pressure side, a connection port with a sealing cap is required to seal off the oxygen inlet port and avoid high pressure gases escaping when the oxygen flow source is not connected. Secondly, in the event that the oxygen source is turned on before the blower is turned on the breathing circuit, humidification chamber and blower become flooded with 100% oxygen. This is likely to create a fire safety risk if sparking should occur within the blower or heated breathing tube when turned on. Thirdly, if the oxygen gases source is added at the outlet of the humidification chamber, the oxygen gas, when mixed with other gases delivered to the patient, lowers the overall humidity of the gases delivered.

SUMMARY OF THE INVENTION

It is an object of the present invention to provide a breathing assistance apparatus that goes some way to overcoming the abovementioned disadvantages or that at least provides the public or industry with a useful choice.

Accordingly in a first aspect the present invention consists in a breathing assistance apparatus adapted to deliver humidified gases to a patient comprising:

a gases supply having an inlet in which gases are drawn through, humidification means including a humidification chamber having an outlet, said gases flowing from said inlet through said humidification chamber and out said outlet, and manifold on or about said gases supply inlet that enables oxygen or other gases to be added to said gases.

Preferably said manifold includes an oxygen inlet port capable of being connected to an oxygen supply.

Preferably said manifold is substantially rectangular.

Preferably said manifold includes at least one aperture to allow the drawing of other gases into said manifold.

Preferably said gases supply includes an internal sensor that is capable of sensing the fraction of oxygen flowing through said breathing assistance apparatus.

Preferably said gases supply includes a controller connected to said internal sensor.

Preferably said gases supply includes a display controlled by said controller and said controller causes said fraction of oxygen to be displayed and updated on said display.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

One preferred form of the present invention will now be described with reference to the accompanying drawings.

DETAILED DESCRIPTION OF THE PREFERRED EMBODIMENTS

The breathing assistance apparatus of the present invention includes a manifold that is preferably provided with or retrofittable to gases supply and humidifying devices. The manifold allows gases from an oxygen concentrator to be combined with the flow through a gases supply and humidifying device, most usually air. The combined output of oxygen and other breathing gases (air) is then humidified.

The breathing assistance apparatus and manifold of the present invention provides a safe method to add oxygen to the input air stream of a gases supply and humidifying device and reduces the amount of accumulation of oxygen within the gases supply device, reducing fire risk should sparking occur within the device.

Figure 1A:
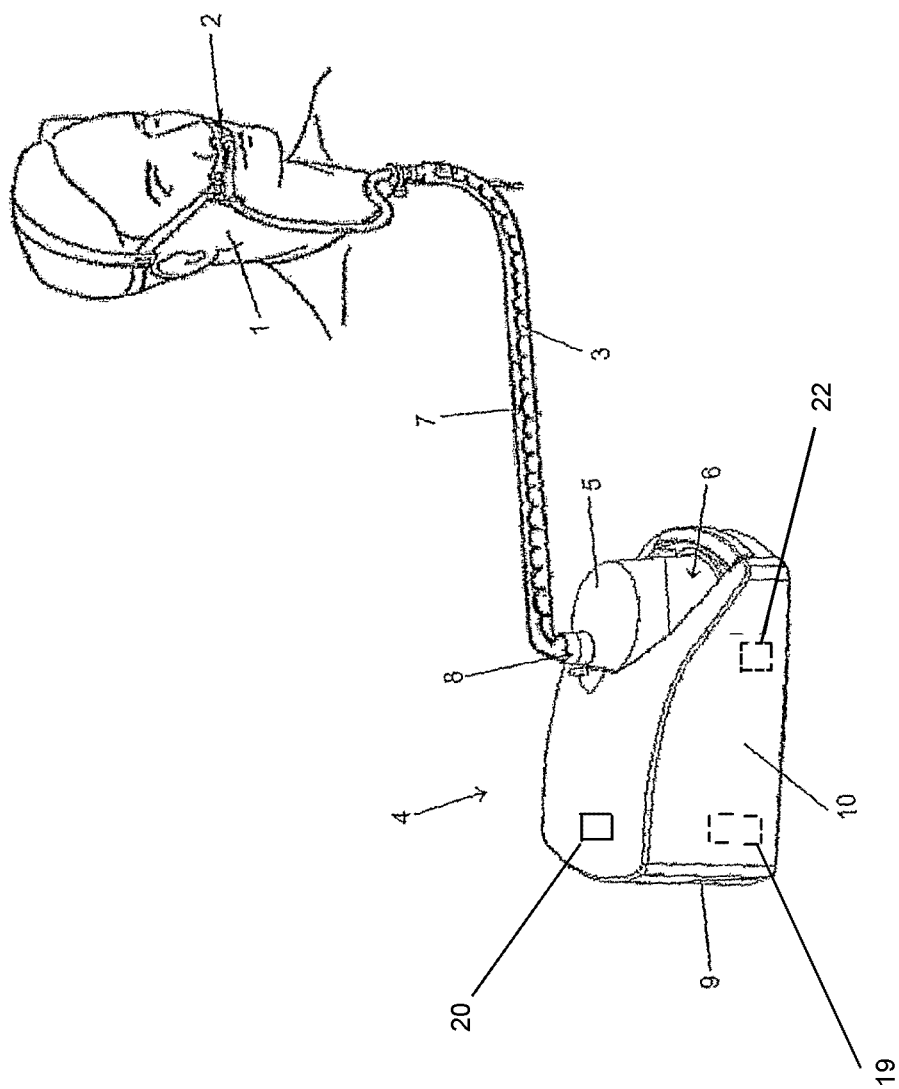
FIGS. 1A-1B are illustrations of the breathing assistance apparatus that may utilize the manifold of the present invention.
Figure 1B:
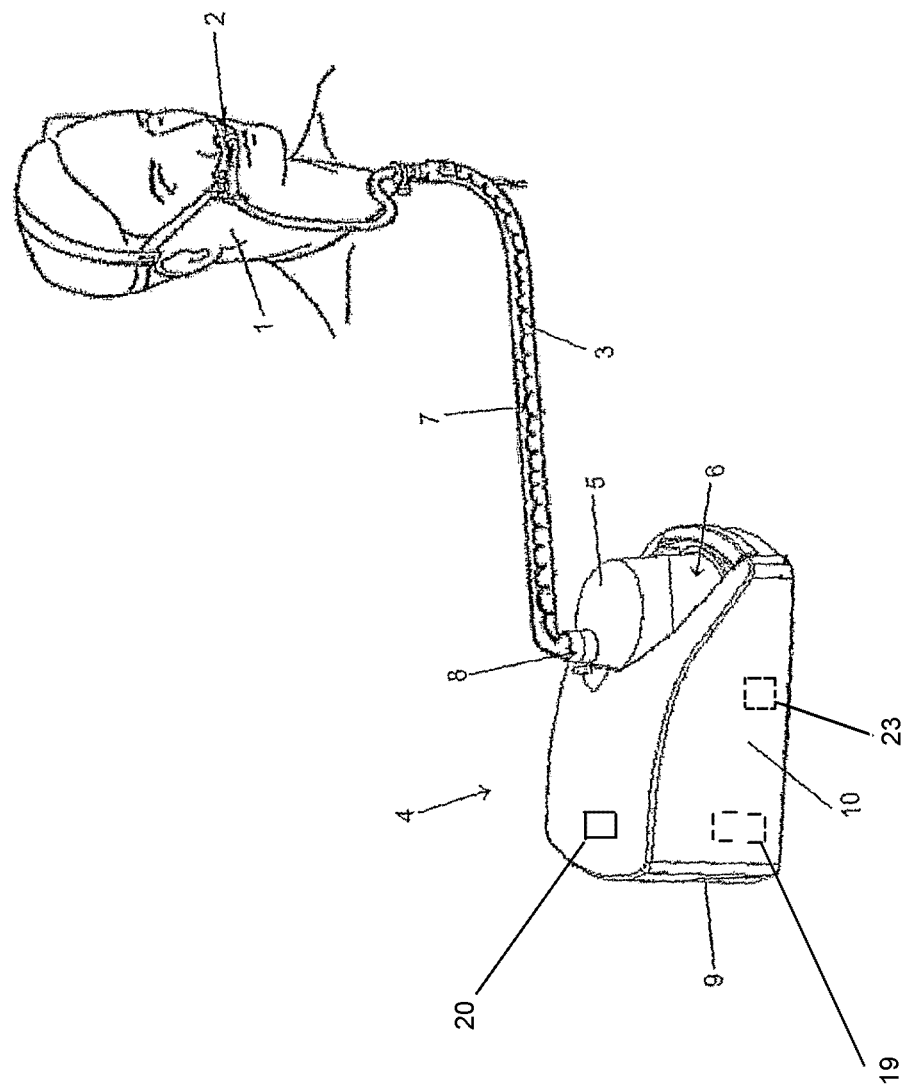

The present invention provides a breathing assistance apparatus where the flow of gases passes in sequence through a gases supply means or flow driver (such as, a blower, fan or compressor), humidification chamber, heated delivery circuit, then to a patient interface, such as that shown in FIG. 1.

Gases are passed to the patient 1 by way of a patient interface 2. The patient interface used with the apparatus of the present invention may be a full-face mask, nasal mask, nasal cannula, oral mouthpiece or tracheostomy connection, but the description below and figures disclose the use of a nasal cannula.

With reference to FIG. 1 the humidification apparatus of the present invention is shown in which a patient 1 is receiving humidified and pressurized gases through nasal cannula 2. The cannula 2 is connected to a gases transportation pathway or inspiratory conduit 3 that in turn is connected to an integrated gases supply and humidifying device 4 (including a humidification chamber 5). In the preferred embodiment of the blower-humidifying device 4, the gases supply or blower is combined in one housing with the humidifier and humidification chamber.

In the preferred embodiment, the humidification chamber 5 extends out from the housing 10 and is capable in use of being removed and replaced (by a slide on movement) by the patient or other user. Also, the inlet port (not shown) to the humidification chamber 5 is internal within the housing 10. It must be appreciated that the embodiment described above in relation to the housing and FIG. 1 merely illustrates one form of the housing of the integrated gases supply and humidifying device. In other forms the gases supply or blower and humidifier may be in separate housings.

The inspiratory conduit 3 is connected to an outlet 8 of the humidification chamber 5 that contains a volume of water 6. Inspiratory conduit 3 contains heating means or heater wires 7 that heat the walls of the conduit to reduce condensation of humidified gases within the conduit and the patient interface (nasal cannula 2). The humidification chamber 5 is preferably formed from a plastics material and may have a highly heat conductive base (for example an aluminum base) that is in direct contact with a heater plate (not shown but located at the base of the chamber 5, within the blower housing). The gases supply and humidifying device 4 is provided with control means or an electronic controller 20 that may comprise a microprocessor based controller executing computer software commands stored in associated memory. The controller 20 receives input from sources such as user input means or dial (not shown) through which a user of the device 4 may, for example, set a predetermined required value (preset value) of humidity or temperature of the gases supplied to patient 1.

In response to the user set humidity or temperature value input via dial (or buttons) and other possible inputs such as internal sensors that sense gases flow or temperature, or by parameters calculated in the controller 20, the controller 20 determines when (or to what level) to energize heater plate to heat the water 6 within humidification chamber 5. As the volume of water 6 within humidification chamber 5 is heated, water vapor begins to fill the volume of the chamber above the water's surface and is passed out of the humidification chamber outlet 8 with the flow of gases (for example air) provided from a blower part of the device that has entered the device 4 through an inlet 9 on the back of the gases supply and humidifying device 4.

The gases supply within the device 4 is preferably a variable speed pump 22 or fan 23 that draws air or other gases through the blower inlet 9. The speed of variable speed pump 22 or fan 23 is preferably controlled by the control means or electronic controller 20 described above in response to inputs entered into the device 4 by the user.

As discussed above it would be advantageous to provide oxygen therapy with humidification therapy to patients that suffer from COPD and other respiratory disorders. The breathing assistance apparatus of the present invention provides this by having a manifold that is attachable to existing gases supply and humidifying devices, such as, the Sleep Style™ 600 series CPAP devices of Fisher & Paykel Healthcare Limited. It must be noted that any CPAP, auto PAP, bi-level or other flow generating device that provides high gases flow and potentially humidification of gases may utilize a manifold as described below. The manifold allows the output from an oxygen concentrator to be combined with the flow from a gases supply and humidifying device and the combined output of oxygen and other breathing gases can then be humidified.

Figure 2:
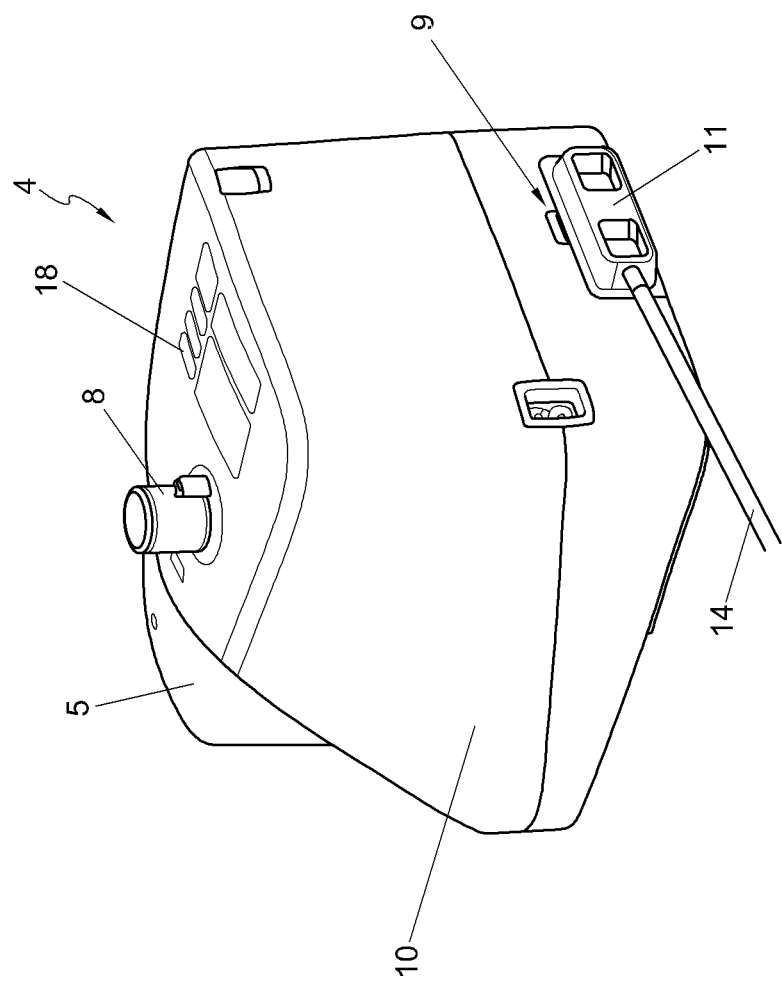
FIG. 2 is a rear view of a blower and humidifier apparatus with a manifold of the present invention installed.
Figure 3:
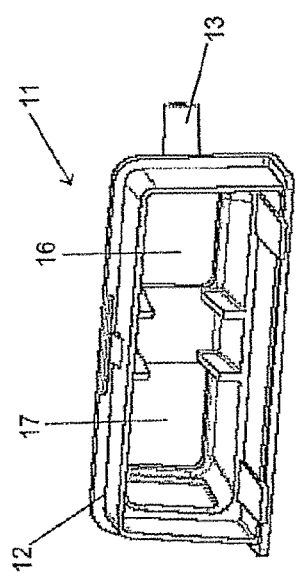
FIG. 3 is a rear view of the manifold of the present invention.
Figure 5:
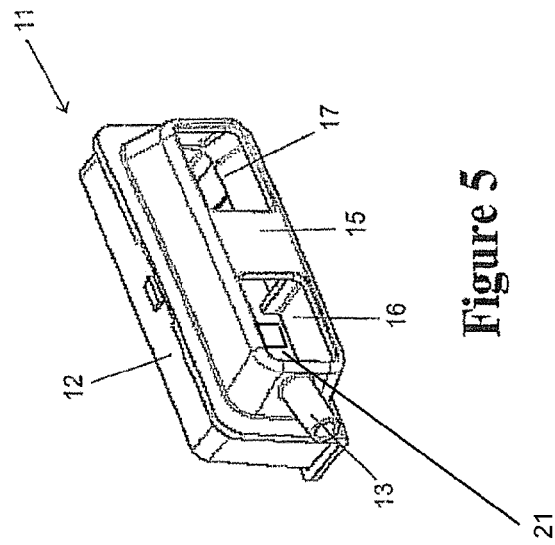
FIG. 5 is a second perspective view of the manifold of FIG. 3.
Figure 4:
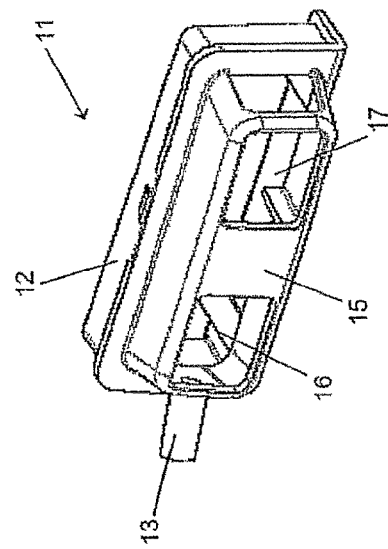
FIG. 4 is a first perspective view of the manifold of FIG. 3.

FIG. 2 shows a gases supply and humidifying device 4 with a manifold 11 installed. The manifold 11 is shown in further detail in FIGS. 3 to 5. The manifold 11 is preferably a substantially rectangular insert that is capable of being inserted into the inlet port 9 on the device 4. The manifold 11 has a recessed edge 12 that fits into a complementary lip on the inlet port 9 and has an oxygen inlet port 13 to which tubing 14 or the like can be attached that feeds to an oxygen supply tank or the like. The oxygen port 13 preferably extends from the side of the manifold 11. The manifold 11 has an extended area 15 that includes at least one aperture (although two apertures 16, 17 are shown in FIGS. 3 to 5). The apertures 16, 17 allow for ambient air to be drawn into the device 4 by the action of the pump 22 or fan 23. The ambient air plus oxygen gases are mixed within the device 4 and exit the chamber outlet 8 as humidified air plus oxygen that is then passed to the patient via the conduit 3.

A filter 21, for example, a substantially rectangular piece of meshed filter material or the like, may be placed inside the apertures 16, 17, such that it fits within the inner part of the extended area 15 and filters all gases entering the blower inlet.

ADVANTAGES

This breathing assistance apparatus and manifold of the present invention provides a safe method to add oxygen to the input air stream of a gases supply and humidifying device. The full oxygen output from the tubing feeding oxygen to the manifold is drawn into the device when the device is in use, but if the device is switched off oxygen that is fed into the manifold disperses through the apertures 16, 17 and therefore remains outside the device 4. Therefore, oxygen does not accumulate within the device (for example, a gases supply such as a blower) and create a fire risk. Consequently, the manifold lowers the fire hazard risk should a spark occur inside the blower or breathing conduit.

By adding oxygen to the inlet of the flow generation device this oxygen can be fully humidified along with the other gases delivered to the patient. Prior art systems usually add oxygen after humidification of gases thus reducing the overall humidification of the gases that reach the patient.

Furthermore, adding oxygen on the inlet side of the flow source makes it possible to sense inside the device 4 the fraction of oxygen in the combined gas flow and display this fraction on a display on the flow source. Therefore, in a further embodiment the gases supply (blower or integrated blower and humidifying device 4) includes an internal sensor 19 that is capable of sensing the fraction of oxygen through the device 4. The internal sensor 19 is preferably connected to the controller 20 within the device (as described above) and the controller 20 causes the fraction of oxygen measurement sensed by the internal sensor 19 to be displayed on the display 18 (see FIG. 2) that is preferably disposed on the top of the device 4. As the fraction of oxygen changes and this is sensed by the internal sensor 19 preferably this change is updated on the display in real time.

The breathing assistance apparatus with the manifold of the present invention does not require one way valves or sealing caps when an oxygen circuit is not connected to the apparatus and is safe and simple for a patient to operate.

What is claimed is:

1. A breathing assistance apparatus adapted to deliver humidified gases to a patient, the breathing assistance apparatus comprising:
   a housing having an inlet port;
   a blower positioned within the housing and configured to draw gases through the inlet port into the housing;
   the apparatus configured to receive a humidification chamber configured to hold a volume of water and to receive gases drawn through the inlet port, the humidification chamber having a heat conductive base configured to transfer heat into the volume of water from a heat source outside of the chamber to produce water vapor to humidify the gases received from the inlet port; and
   a manifold attachable to an area of the housing surrounding the inlet port, the manifold comprising:
      a first wall and a second wall extending at an angle from the first wall;
      an auxiliary gases port extending from the first wall and configured to be connected to an auxiliary gases supply; and
      at least one aperture defined by the second wall and configured to allow ambient gases to be drawn into the inlet port such that ambient gases pass through the manifold before entering the inlet port;
      wherein the manifold is configured to add auxiliary gases received from the auxiliary gases supply to the ambient gases drawn through the at least one aperture into the inlet port when the device is delivering gases to the patient.

2. The breathing assistance apparatus of claim 1, wherein the auxiliary gases supply comprises an oxygen supply and the auxiliary gases port is configured to connect to tubing that delivers oxygen to the manifold.

3. The breathing assistance apparatus of claim 2, wherein attachment of the manifold to the apparatus enables use of the apparatus to provide oxygen therapy to the patient.

4. The breathing assistance apparatus of claim 1, wherein attachment of the manifold to the apparatus enables the apparatus to combine auxiliary gases with ambient gases into combined gases, humidify the combined gases, and deliver the combined gases to the patient.

5. The breathing assistance apparatus of claim 1, wherein the manifold is configured to disperse auxiliary gases received from the auxiliary gases supply through the at least one aperture to outside the apparatus when the apparatus is not delivering gases to the patient and the dispersion of auxiliary gases through the at least one aperture to outside the apparatus inhibits accumulation of auxiliary gases within the apparatus.

6. The breathing assistance apparatus of claim 1, wherein the apparatus comprises a single gases inlet port and attachment of the manifold to the apparatus enables use of the apparatus to deliver combined ambient gases and auxiliary gases to the patient.

7. The breathing assistance apparatus of claim 1, further comprising a filter disposed within the manifold to filter gases entering the inlet port.

8. The breathing assistance apparatus of claim 1, wherein the manifold comprises a substantially rectangular insert configured to be inserted into the inlet port.

9. The breathing assistance apparatus of claim 1, wherein the manifold comprises a recessed edge configured to fit into a complementary lip of the apparatus.

10. The breathing assistance apparatus of claim 1, wherein the auxiliary gases port extends from a side of the manifold relative to the at least one aperture.

11. The breathing assistance apparatus of claim 10, wherein ambient gases are drawn through the at least one aperture into the inlet port along a substantially linear flow path and the auxiliary gases port extends from a lateral side of the manifold relative to the substantially linear flow path.

12. The breathing assistance apparatus of claim 1, wherein the manifold is configured to be retrofit to the breathing assistance apparatus.

13. The breathing assistance apparatus of claim 1, wherein the blower and at least part of the humidification chamber are provided in the housing and the inlet port is configured to supply gases to the blower through the housing.

14. The breathing assistance apparatus of claim 1 wherein the second wall opposes the inlet port such that an axis extends through the at least one aperture into the inlet port.

15. The breathing assistance apparatus of claim 1 further comprising an internal sensor configured to sense a fraction of oxygen flowing through said breathing assistance apparatus.

16. The breathing assistance apparatus of claim 1, wherein the manifold is a single piece.

17. A device adapted to deliver humidified gases to a patient, the device comprising:
  a housing comprising an inlet port;
  a blower positioned inside of the housing and configured to draw gases into the housing through the inlet port in use;
  the device configured to receive a humidification chamber configured to hold a volume of water and receive gases drawn through the inlet port, the humidification chamber having a heat conductive base configured to transfer heat into the volume of water from a heat source outside of the chamber to produce water vapor to humidify the gases received from the inlet port; and
  a manifold configured to be coupled to the housing about the inlet port, the manifold comprising an outlet, a mounting portion configured to be coupled to the housing, and a protruding portion, the protruding portion comprising at least one inlet aperture, the outlet configured to be in fluid communication with the inlet port of the housing in use and the at least one inlet aperture configured to allow ambient gases to be drawn into the manifold and then the inlet port; the protruding portion comprising an auxiliary port configured to be connected to an auxiliary gases supply;
  wherein the manifold is configured to add auxiliary gases received from the auxiliary gases supply to the ambient gases drawn through the at least one inlet aperture when the device is delivering gases to the patient.

18. The device of claim 17, wherein the ambient gases are drawn into the at least one inlet aperture and out of the outlet into the inlet port of the device along a substantially linear flow path and the auxiliary port extends from a side of the manifold normal to the substantially linear flow path.

19. The device of claim 18 further comprising a side aperture diametrically opposed to the auxiliary port, the side aperture configured to disperse the auxiliary gases outside the device when the device is not delivering gases to the patient.

* * * * *